(12) United States Patent
Maruyama (10) Patent No.: US 7,846,089 B2
(45) Date of Patent: Dec. 7, 2010

(54) BENDABLE PORTION CONTROL MECHANISM OF AN ENDOSCOPE

(75) Inventor: Yoshinori Maruyama, Saitama (JP)

(73) Assignee: Hoya Corporation, Tokyo (JP)

( * ) Notice: Subject to any disclaimer, the term of this patent is extended or adjusted under 35 U.S.C. 154(b) by 765 days.

(21) Appl. No.: 11/758,870

(22) Filed: Jun. 6, 2007

(65) Prior Publication Data
US 2007/0287887 A1 Dec. 13, 2007

(30) Foreign Application Priority Data
Jun. 8, 2006 (JP) ............... 2006-159257

(51) Int. Cl.
*A61B 1/00* (2006.01)
(52) U.S. Cl. .................... 600/147; 148/146
(58) Field of Classification Search ............ 600/106, 600/118, 139, 141, 142, 146–148
See application file for complete search history.

(56) References Cited

U.S. PATENT DOCUMENTS

| 4,825,850 | A | * | 5/1989 | Opie et al. ........... 600/122 |
| 5,007,406 | A | * | 4/1991 | Takahashi et al. ........... 600/119 |
| 5,762,067 | A | * | 6/1998 | Dunham et al. ........... 600/462 |
| 2001/0034472 | A1 | * | 10/2001 | Fujii et al. ........... 600/146 |

FOREIGN PATENT DOCUMENTS

| JP | 6 327613 | 11/1994 |
| JP | 9 98942 | 4/1997 |
| JP | 10 286220 | 10/1998 |
| JP | 11 047082 | 2/1999 |

OTHER PUBLICATIONS

English Language Abstract of JP 9-98942.
English Language Abstract of JP 6-327613.
English Language Abstract of JP 10-286220.
English Language Abstract of JP 11-047082.
U.S. Appl. No. 11/737,291, to Maruyama, filed Apr. 19, 2007.
U.S. Appl. No. 11/737,331, to Maruyama, filed Apr. 19, 2007.

* cited by examiner

*Primary Examiner*—Thomas J Sweet
*Assistant Examiner*—Ryan Henderson
(74) *Attorney, Agent, or Firm*—Greenblum & Bernstein P.L.C.

(57) ABSTRACT

A bendable portion control mechanism of an endoscope including a control portion and an insertion portion, includes two manually-rotatable control knobs, one of which being provided on top of the other and disposed coaxially with each other, for bending the bendable portion in two orthogonal directions, each of the control knobs including a water-sealed internal space; and two bent state holding mechanisms, provided in the two water-sealed internal spaces, respectively, for holding a bent state of the bendable portion in the two orthogonal directions by exerting frictional resistance on rotating operations of the two control knobs. The two control knobs detach from and attach to the control portion without interfering with the two bent state holding mechanisms so that it is possible to adjust operational characteristics of each of the two bent state holding mechanisms upon detaching the two control knobs, respectively.

9 Claims, 8 Drawing Sheets

Fig.8

BENDABLE PORTION CONTROL MECHANISM OF AN ENDOSCOPE

BACKGROUND OF THE INVENTION

1. Field of the Invention

The present invention relates to a bendable portion control mechanism of an endoscope.

2. Description of the Related Art

A typical endoscope with a bendable portion capable of being freely bent in four directions (upward, downward, leftward and rightward) is provided with a U-D control knob for bending the bendable portion upward and downward, an R-L control knob for bending the bendable portion rightward and leftward, a U-D bent state holding mechanism for holding a bent state of the bendable portion in the upward/downward direction by exerting frictional resistance on the rotating operation of the U-D control knob, and an R-L bent state holding mechanism for holding a bent state of the bendable portion in the rightward/leftward direction by exerting frictional resistance on the rotating operation of the R-L control knob in the control portion of the endoscope. The U-D control knob and the R-L control knob are coaxially arranged so that one thereof is provided on top of the other, so that each of the U-D control knob and the R-L control knob can be freely rotated on a common axis, and are installed in water-sealed spaces together with the U-D bent state holding mechanism and the R-L bent state holding, respectively, to prevent the entry of water from the outside the endoscope. This structure is disclosed in, e.g., Japanese unexamined patent publications H09-98942, H06-327613, H10-286220 and H11-47082.

In endoscopes provided with such bent state holding mechanisms to hold a bent state of the bendable portion, it is necessary to make an adjustment to the operational characteristics of each bent state holding mechanism (e.g., to make an adjustment to the degree of frictional resistance produced by the bent state holding mechanism) by checking whether or not the bendable portion is in an appropriate bent state with the bendable portion being bent by rotating the associated control knob.

However, since bent state holding mechanisms for endoscopes produced in recent years are installed in the water-sealed space of the associated control knob which is water-sealed to prevent entry of water from outside the endoscope, considering that the endoscope is washed and sterilized after use by steam or a liquid medicine, each control knob needs to be removed if it is desired adjust the operational characteristics of each bent state holding mechanism.

Nevertheless, to remove the U-D control knob or the R-L control knob (one which is provided on top of the other and coaxially arranged) which is positioned closest to the base of the control portion, the bent state holding mechanism installed in this other control knob needs to be disassembled.

Accordingly, it is troublesome to make an adjustment to the degree of frictional resistance which is exerted on the rotating operation of the control knob positioned closer to the base of the control portion; moreover, a need to make an adjustment to the degree of frictional resistance which is exerted on the rotating operation of the other control knob that is positioned farther from the base of the control portion arises after the control knob positioned closer to the base of the control portion is re-mounted to the control portion. Therefore, fine adjustments made to the endoscope during assembly of the endoscope after the bendable portion control mechanism is assembled and adjustments made to the endoscope during routine maintenance after use by the operator are very troublesome and time-consuming.

SUMMARY OF THE INVENTION

The present invention provides a bendable portion control mechanism of an endoscope provided with two bent state holding mechanisms which are respectively installed in the water-sealed spaces of two control knobs, one of the which being provided on top of the other and coaxially arranged, wherein adjustments to operational characteristics of the bent state holding mechanisms can be made easily with a small number of man-hours in a short amount of time.

According to an aspect of the present invention, a bendable portion control mechanism of an endoscope is provided, including a control portion and an insertion portion extending from the control portion, the insertion portion having a bendable portion, the bendable portion control mechanism including two manually-rotatable control knobs, one of the manually-rotatable control knobs being provided on top of the other thereof and disposed coaxially with each other on the control portion, for bending the bendable portion in two orthogonal directions, each of the control knobs including a water-sealed internal space; and two bent state holding mechanisms, provided in the two water-sealed internal spaces, respectively, for holding a bent state of the bendable portion in the two orthogonal directions by exerting frictional resistance on rotating operations of the two control knobs. The two control knobs are configured to be detached from and attached to the control portion without interfering with any element of the two bent state holding mechanisms. It is possible to adjust operational characteristics of each of the two bent state holding mechanisms upon detaching the two control knobs, respectively.

The bendable portion control mechanism can include a first bending drive disk mounted to the control portion to be freely rotatable, wherein one of the control knobs which is positioned closest to a base of the control portion is disengageably engaged with an outer peripheral part of the first bending drive disk in a direction of a common rotational axis of the control knobs, and the one of the control knobs is fixed to the first bending drive disk by a retaining nut which is screw-engaged with an outer peripheral part of the first bending drive disk.

The bendable portion control mechanism can include a second bending drive disk mounted to the control portion to be freely rotatable, wherein the other of the control knobs is engaged with an outer peripheral part of the second bending drive disk to be freely disengaged therefrom in the direction of the common rotation axis of the control knobs, and the one of the control knobs and the retaining nut are formed so that inner diameters thereof are greater than an outer diameter of the second bending drive disk and an outer diameter of one of the two bent state holding mechanisms which is positioned in the other of the control knobs.

It is desirable for one of the two bent state holding mechanisms, which is positioned in one of the control knobs which is positioned closest to a base of the control portion, to include a performance characteristic adjusting member for exerting frictional resistance on the rotating operation of the one of the control knobs, and for the performance characteristic adjusting member to be outwardly exposed when the one of the control knobs is detached.

The bendable portion control mechanism can include at least two control wires, distal ends of which are fixed to the bendable portion, and are extended to the control portion through the insertion portion. The two control knobs pull the two control wires to bend the bendable portion in the two orthogonal directions, respectively, when manually-rotated.

The bendable portion control mechanism can include a stationary cylindrical shaft which extends upright from the control portion to be coaxial with the common rotational axis of the two control knobs; and a tubular drive shaft positioned over the stationary cylindrical shaft to be freely rotatable on an axis of the stationary cylindrical shaft. The first bending drive disk is formed integral with the tubular drive shaft.

The bendable portion control mechanism can include a stationary cylindrical shaft which extends upright from the control portion to be coaxial with the common rotational axis of the two control knobs; an inner tubular drive shaft positioned over the stationary cylindrical shaft to be freely rotatable on an axis of the stationary cylindrical shaft; and an outer tubular drive shaft positioned over the inner tubular drive shaft to be freely rotatable on the axis of the stationary cylindrical shaft. The first bending drive disk and the second bending drive disk are formed integral with the outer tubular drive shaft and the inner tubular drive shaft, respectively.

It is desirable for the first bending drive disk and the second bending drive disk to be positioned between the two control knobs so as to face each other.

It is desirable for the bendable portion control mechanism to include at least one O-ring positioned between the first bending drive disk and the one of the two control knobs to seal the water-sealed internal space thereof in a watertight fashion.

It is desirable for the bendable portion control mechanism to include at least one O-ring positioned between the first bending drive disk and the one of the two control knobs to seal the water-sealed internal space thereof in a watertight fashion; and at least one O-ring positioned the second bending drive disk and the other of the two control knobs to seal the water-sealed internal space thereof in a watertight fashion.

According to the present invention, since the bendable portion control mechanism is configured to allow the control knobs to be detached from and attached to the control portion while preventing the control knobs from interfering with any element of the two bent state holding mechanisms, to thereby make it possible to adjust the operational characteristics of each of the two bent state holding mechanisms simply by detaching the two control knobs, adjustments to operational characteristics of the two bent state holding mechanisms (especially the bent state holding mechanism which is positioned in the water-sealed internal space of one of the two control knobs which is positioned closest the base of the control portion) can be made easily with a small number of man-hours in a short amount time.

The present disclosure relates to subject matter contained in Japanese Patent Application No. 2006-159257 (filed on Jun. 8, 2006), which is expressly incorporated herein in its entirety.

BRIEF DESCRIPTION OF THE DRAWINGS

The present invention will be described below in detail with reference to the accompanying drawings in which.

DESCRIPTION OF THE PREFERRED EMBODIMENT

Figure 2:
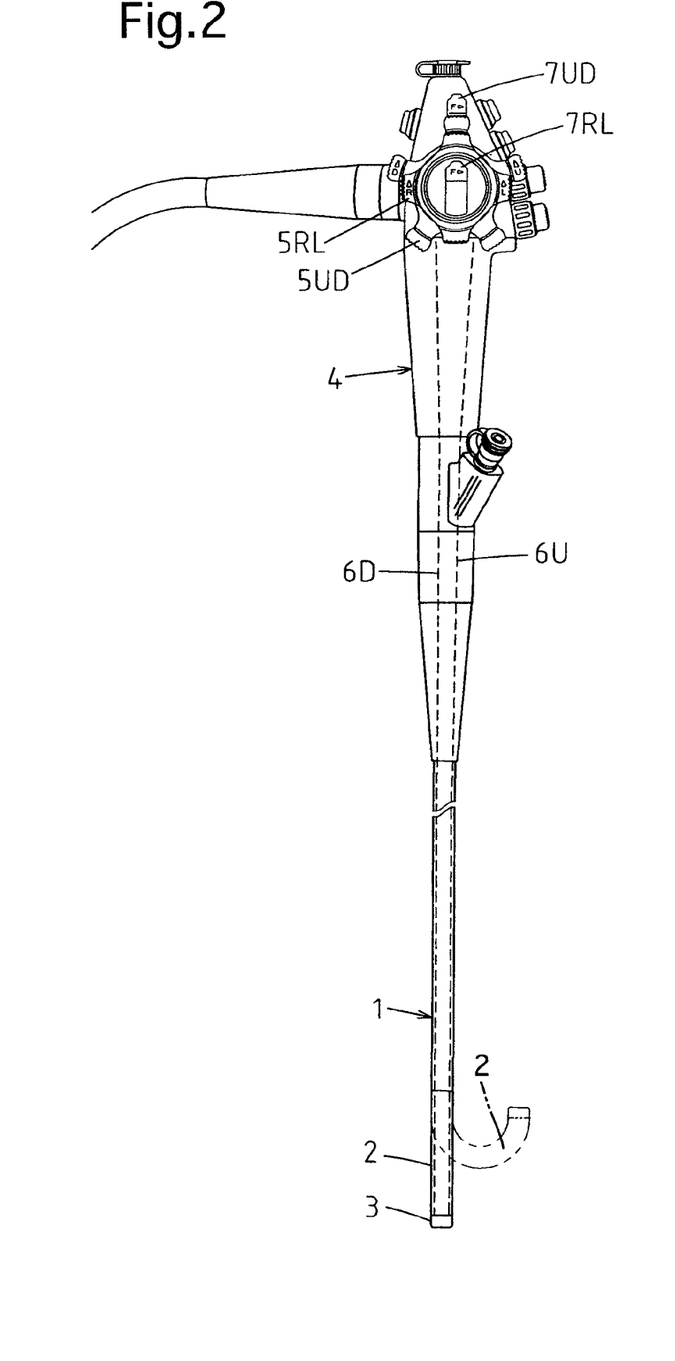
FIG. 2 is an external view of the endoscope, showing the overall structure thereof.

FIG. 2 shows the general configuration of an embodiment of the electronic endoscope, in which an image captured thereby is displayed on a monitoring screen (not shown). The endoscope is provided with a flexible insertion portion 1 and a control portion 4 coupled to the proximal end of the insertion portion 1. The insertion portion 1 is provided in the vicinity of the distal end (free end) thereof with a remote-controllable bendable portion 2, and is further provided with an end body 3 fixed to the end (free end) of the bendable portion 2. An objective window and others (not shown) are provided in the end body 3.

The control portion 4, which is coupled to the proximal end of the insertion portion 1, is provided thereon with a U-D control knob 5UD for bending the bendable portion 2 upward and downward and an R-L control knob 5RL for bending the bendable portion 2 rightward and leftward. The R-L control knob 5RL is provided on top of the U-D control knob 5UD and are coaxially arranged so that each of the U-D controls knob 5UD and the R-L control knob 5RL can be freely rotated on a common axis.

An upward-direction control wire 6U (see FIG. 2) and a downward-direction control wire 6D (see FIG. 2) are inserted into the insertion portion 1 and distal ends thereof and are fixed to the end body 3. Turning the U-D control knob 5UD counterclockwise causes the upward-direction control wire 6U to be pulled toward the control portion 4 to thereby cause the bendable portion 2 to bend upward (e.g., upward direction of a monitoring screen of the endoscope which corresponds to forward direction of the control portion 4) as shown by two-dot chain lines in FIG. 2. Turning the U-D control knob 5UD clockwise causes the downward-direction control wire 6D to be pulled toward the control portion 4 to thereby cause the bendable portion 2 to bend downward.

Additionally, turning the R-L control knob 5RL counterclockwise causes a leftward-direction control wire (not shown), which is inserted into the insertion portion 1 to be installed therein, to be pulled toward the control portion 4 to thereby cause the bendable portion 2 to bend leftward. Turning the R-L control knob 5RL clockwise causes a rightward-direction control wire (not shown), which is installed in the insertion portion 1, to be pulled toward the control portion 4 to thereby cause the bendable portion 2 to bend rightward. In this manner, the bendable portion 2 can be remote-controlled to be bent freely in any directions at any angle from the control portion 4 side.

The control portion 4 is provided with a U-D bent state holding knob 7UD which is operated to hold the U-D control knob 5UD at any given rotation position, and an R-L bent state holding knob 7RL which is operated to hold the R-L control knob 5RL at any given rotation position. The U-D bent state holding knob 7UD and the R-L bent state holding knob 7RL are arranged to be capable of being operated to rotate coaxially with the U-D control knob 5UD and the R-L control knob 5RL.

Figure 3:
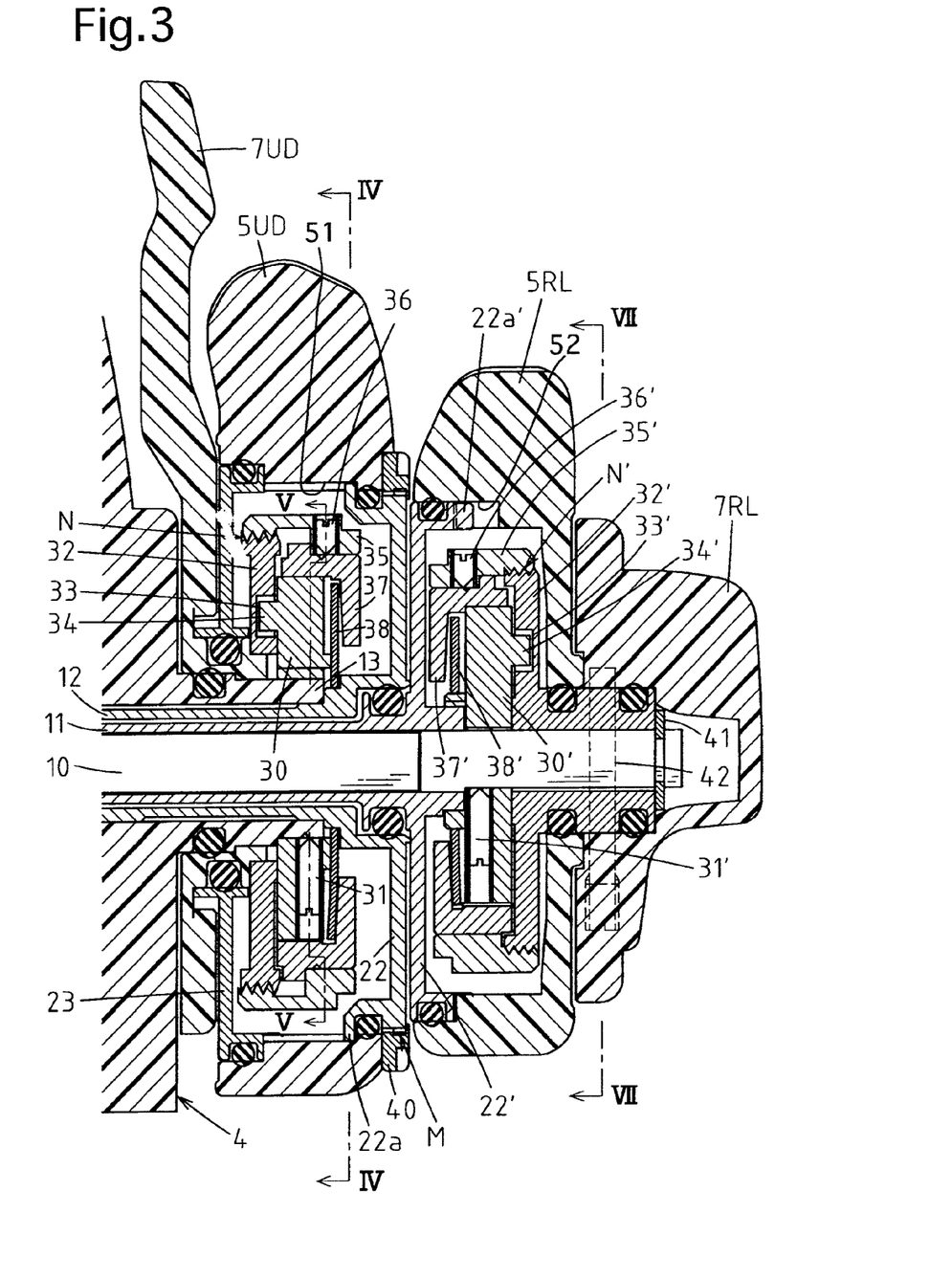
FIG. 3 is an axial cross sectional view of the bendable portion control mechanism of the endoscope shown in FIG. 2.

The present embodiment of the endoscope is provided with a bendable portion control mechanism consisting of two mechanisms: a bendable portion U-D control mechanism and a bendable portion R-L control mechanism. FIG. 3 shows the bendable portion U-D control mechanism, installed onto the control portion 4 in a freely rotatable manner, for bending the bendable portion 2 vertically, and the bendable portion R-L control mechanism, installed onto the control portion 4 in a freely rotatable manner, for bending the bendable portion 2 laterally. The U-D bent state holding knob 7UD, the U-D control knob 5UD, the R-L control knob 5RL and the R-L bent state holding knob 7RL are laid one on top of the other in that order and are coaxially arranged.

The U-D control knob 5UD is formed so that a ring-shaped control portion thereof has a large internal space which is sealed with O-rings in a watertight fashion to prevent the entry of water into the internal space from the outside thereof. Likewise, the R-L control knob 5RL is formed so that a ring-shaped control portion thereof has a large internal space which is sealed with O-rings in a watertight fashion to prevent the entry of water into the internal space from the outside thereof. It should be noted that such O-rings are shown in a state before they are resiliently deformed in the drawings for the purpose of illustration and that no reference numeral or sign is affixed to such O-rings in the drawings.

The control portion 4 is provided with a supporting column (cylindrical shaft) 10 which is fixed to an internal frame (not shown) of the control portion 4 to extend outwards uprightly and coaxially with the common axis of the U-D control knob 5UD, the R-L control knob 5RL, the U-D bent state holding knob 7UD and the R-L bent state holding knob 7RL.

The control portion 4 is provided with an R-L tubular drive shaft 11 which is fixed at one end thereof to an R-L pulley (not shown) around which the proximal ends of a leftward-direction control wire (not shown) and a rightward-direction control wire (not shown) are wound. The R-L tubular drive shaft 11 is rotatably fitted on the supporting column 10 and projects outwards (upwards as viewed in FIG. 3) from the control portion 4.

The control portion 4 is provided with a U-D tubular drive shaft 12 which is fixed at one end thereof to a U-D pulley (not shown) around which the proximal ends of the upward-direction control wire 6U and the downward-direction control wire 6D are wound. The U-D tubular drive shaft 12 is rotatably fitted on the R-L tubular drive shaft 11 and rotatably fitted in a cylindrical U-D bearing 13 which is fixed at the base end thereof to the aforementioned internal frame of the control portion 4. The U-D tubular drive shaft 12 projects outwards (upwards as viewed in FIG. 3) from the control portion 4.

Rotating the U-D tubular drive shaft 12 about the axis thereof (the axis of the supporting column 10) causes the aforementioned U-D pulley to rotate to thereby pull one of the upward-direction control wire 6U and the downward-direction control tire 6D to bend the bendable portion 2 upward and downward, respectively, in accordance the direction of rotation of the U-D tubular drive shaft 12. Likewise, rotating the R-L tubular drive shaft 11 about the axis thereof (the axis of the supporting column 10) causes the aforementioned R-L pulley to rotate to thereby pull one of the rightward-direction control wire and the leftward-direction control wire to bend the bendable portion 2 rightward and leftward, respectively, in accordance the direction of rotation of the R-L tubular drive shaft 11.

The U-D tubular drive shaft 12 is provided at the outer end thereof (upper end as viewed in FIG. 3) with a U-D-bending drive disk (first bending drive disk) 22 formed as an integral part of the U-D tubular drive shaft 12. The U-D-bending drive disk 22 has a sufficient size to fully close an outward opening (upper opening as viewed in FIG. 3) of the U-D control knob 5UD that is positioned on the outward side (upper side as viewed in FIG. 3) of the internal space of the U-D control knob 5UD.

The U-D control knob 5UD is engaged with an outer peripheral part of the U-D-bending drive disk 22 to be freely disengageable therefrom in the axial direction of the supporting column 10. A retaining nut 40 which is screw-engaged with an outer peripheral part of the U-D-bending drive disk 22 at a screw-engaging portion M (see FIGS. 1 and 3) presses the U-D control knob 5UD against the U-D-bending drive disk 22 to fix the U-D control knob 5UD to the U-D-bending drive disk 22.

Figure 4:
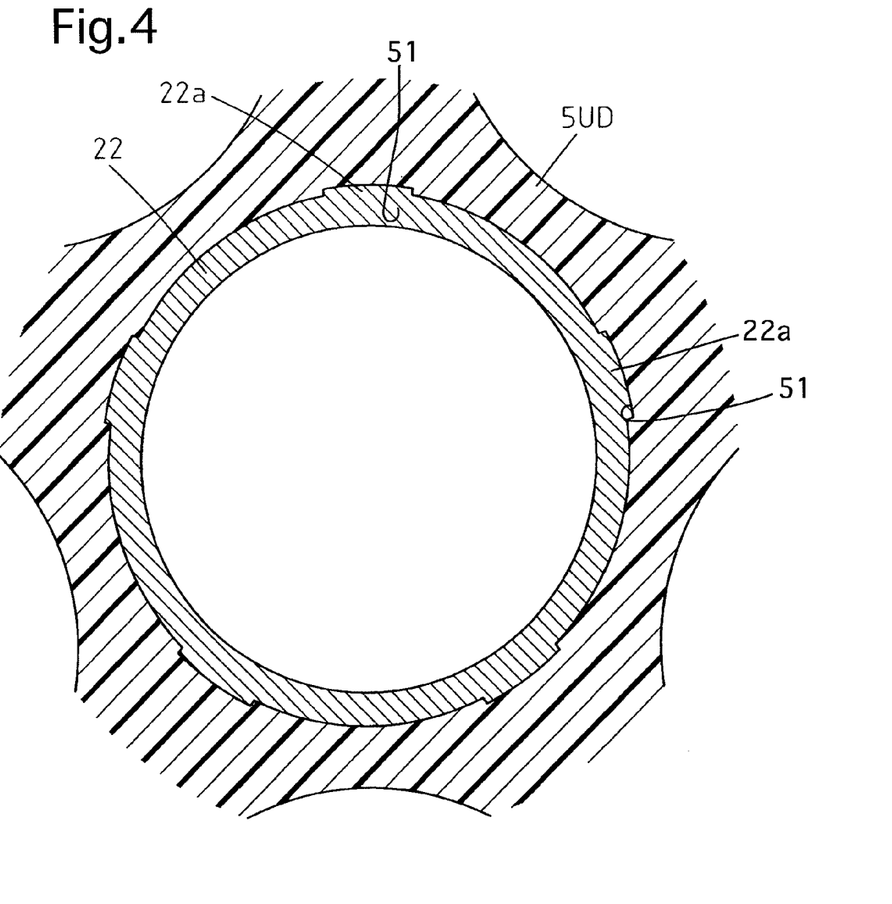
FIG. 4 is a cross sectional view taken along the IV-IV line shown in FIG. 3.

As also shown in FIG. 4, which shows a cross sectional view taken along IV-IV line shown in FIG. 3, the U-D-bending drive disk 22 is provided on the outer periphery thereof with a plurality of projections 22a which project radially outwards to be slidably engaged in a plurality of axial grooves 51, respectively, which are formed on an inner peripheral surface of the U-D control knob 5UD to be parallel to the axis thereof.

Due to the engagements of the plurality of projections 22a with the plurality of axial grooves 51, respectively, the U-D control knob 5UD rotates with the U-D-bending drive disk 22 (and the U-D tubular drive shaft 12). If the retaining nut 40 is removed from the U-D-bending drive disk 22, the U-D control knob 5UD can freely move in the axial direction thereof relative to the U-D-bending drive disk 22 while sliding on the U-D-bending drive disk 22. The control portion 4 is provided between the U-D bent state holding knob 7UD and the U-D control knob 5UD with a disk lid 23 which closes an inward opening (lower opening as viewed in FIG. 3) of the U-D control knob 5UD that is positioned on the inward side (lower side as viewed in FIG. 3) of the internal space of the U-D control knob 5UD.

Reference numerals 30 through 38 shown in FIG. 3 designate elements of a U-D bent state holding mechanism which exerts frictional resistance on the rotating operation of the bendable portion U-D control mechanism to hold the bendable portion U-D control mechanism (which includes the U-D control knob 5UD, and the U-D tubular drive shaft 12 and the U-D-bending drive disk 22 connected to the U-D control knob 5UD) at any given rotation position.

The elements 30 through 38 of the U-D bent state holding mechanism are accommodated and arranged in the internal space of the U-D control knob 5UD which is sealed with O-rings in a watertight fashion to prevent the entry of water into the internal space from the outside. The U-D bent state holding mechanism can operate to exert friction on the rotating operation of the bendable portion U-D control mechanism and to stop exerting the same thereon by operating the U-D bent state holding knob 7UD.

Figure 5:
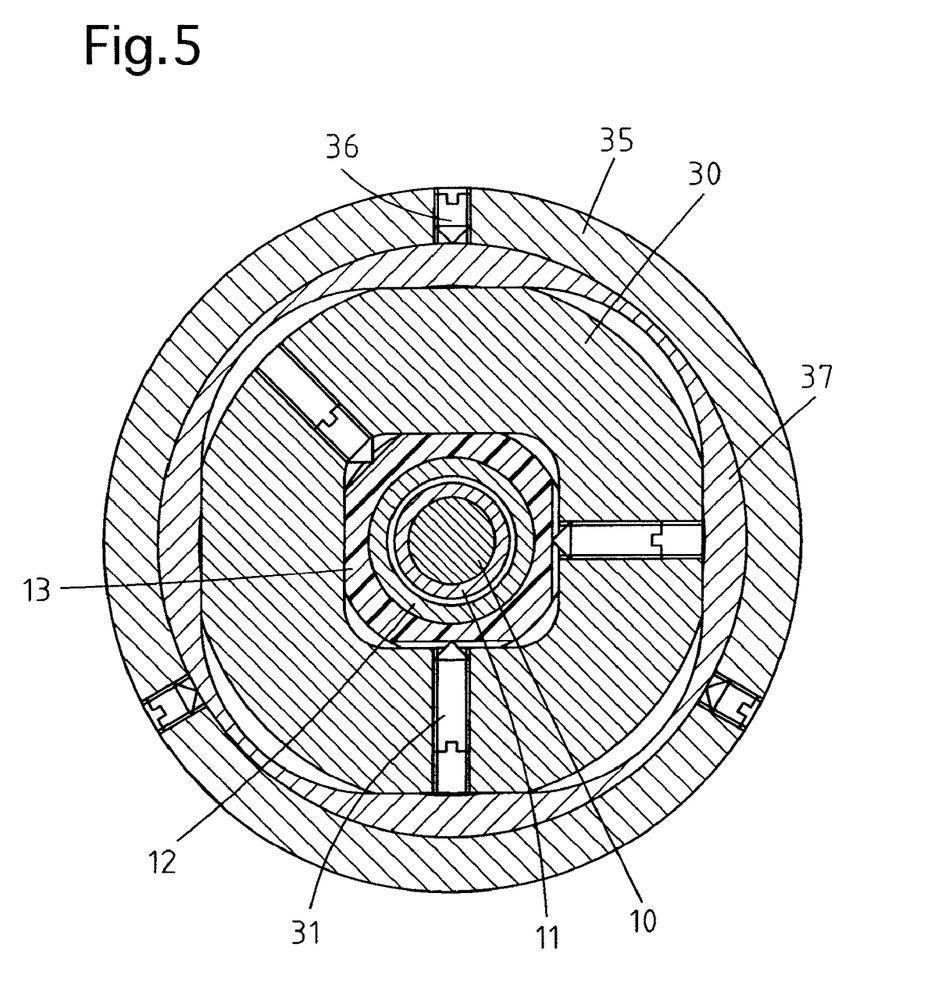
FIG. 5 is a cross sectional view taken along the V-V line shown in FIG. 3.

As also shown in FIG. 5, which shows a cross sectional view taken along V-V line shown in FIG. 3, an immovable base 30 is secured to the U-D bearing 13 (having been fixed to the control portion 4) in the vicinity of the top end thereof by set screws 31.

As shown in FIG. 3, the U-D bent state holding knob 7UD is fitted on an outer peripheral surface of the U-D bearing 13 to be freely rotatable thereon. A male screw ring 32 having a male screw thread on an outer peripheral surface (N) thereof is provided in a central portion of the male screw ring 32 with a polygonal-shaped hole while the U-D bent state holding knob 7UD is provided in a central portion thereof with a corresponding polygonal-shaped shaft portion which is fixedly fitted in the polygonal-shaped hole of the male screw ring 32 so that the male screw ring 32 rotates with the U-D bent state holding knob 7UD.

The range of rotation of the U-D bent state holding knob 7UD (i.e., the range of rotation of the male screw ring 32) is fixed by an arc-shaped groove 33 which is made in the male screw ring 32 and a stop pin 34 which projects from the immovable base 30 to be engaged in the arc-shaped groove 33 (see FIG. 3).

A female screw ring 35 is screw-engaged with the male screw ring 32. A female screw thread of the female screw ring 35 which is screw-engaged with the male screw thread of the male screw ring 32 is formed on a substantially lower-half of the inner peripheral surface of the female screw ring 35. The letter "N" shown in FIGS. 1 and 3 designates the portion of screw-engagement between the female screw thread of the female screw ring 35 and the male screw thread of the male screw ring 32. A metal disk 37 is positioned inside an upper half portion of the female screw ring 35 and fixed integrally thereto by three set screws 36 (see FIG. 5).

The metal disk 37 is made of, e.g., brass, stainless steel, or the like. As shown in FIG. 5, the metal disk 37 has a substantially square central hole, and an inner peripheral surface of the metal disk 37 is partly engaged in an outer peripheral surface of the immovable base 30 at substantially equi-angular intervals of 90 degrees in a manner to allow the metal disk 37 to move in the axial direction relative to the immovable base 30 while preventing the metal disk 37 from rotating about the axis thereof relative to the immovable base 30. Therefore, the female screw ring 35, which moves with the metal disk 37, is also freely movable in the axial direction though not rotatable about the axis of the female screw ring 35.

Figure 6:
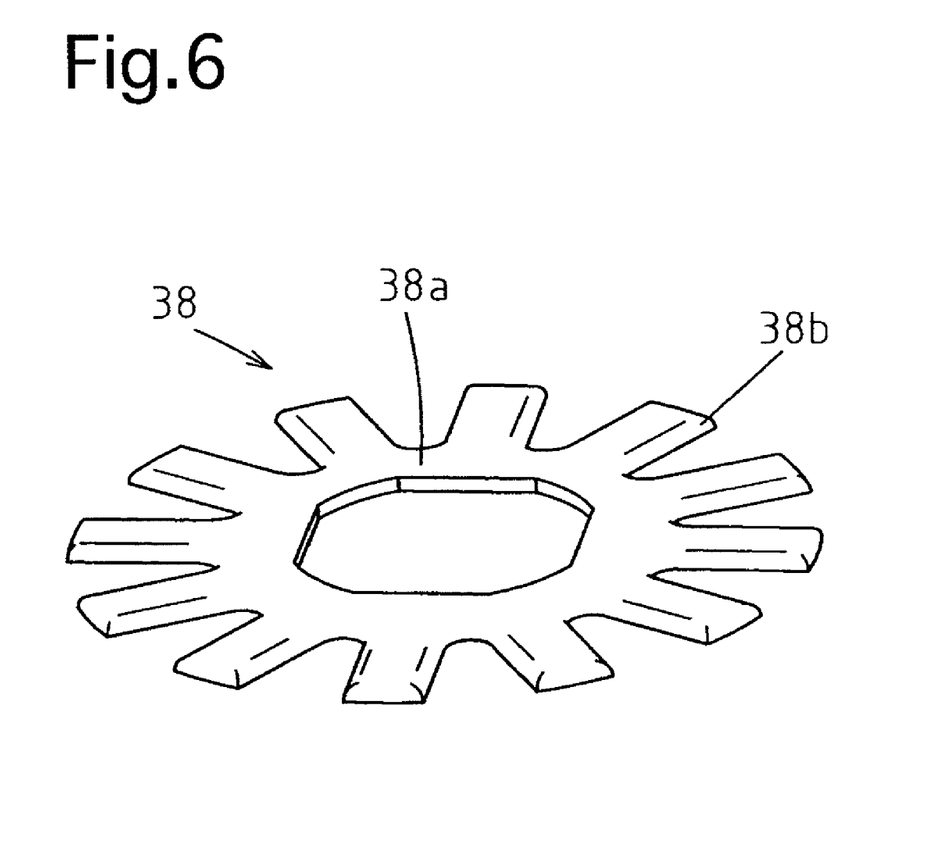
FIG. 6 is a perspective view of a radial plate spring shown in FIG. 3.

As shown in FIG. 3, a radial plate spring 38 made of a resilient metal plate such as a spring stainless steel is installed in the internal space of the U-D control knob 5UD. As shown in FIG. 6, the radial plate spring 38 is provided with a ring portion 38a and a plurality of radial projections (radial leaf springs) 38b which are formed integral with the ring portion 38a to project radially outwards from the ring portion 38a. The radial plate spring 38 is formed in a flat shape as a whole, and is provided at a center of the ring portion 38a with a substantially square hole.

As shown in FIG. 3, the radial plate spring 38 is engaged at the square hole thereof with a portion of the U-D tubular drive shaft 12 in the vicinity of the upper end thereof to rotate with the U-D tubular drive shaft 12 about the axis thereof. The back of the ring portion 38a of the radial plate spring 38 is in contact with the upper end surface of the immovable base 30 to be supported thereby. An annular surface of the metal disk 37 which is located at a position facing the plurality of radial projections 38b of the radial plate spring 38 is formed as an oblique surface which is brought to be pressed obliquely against upper flat surfaces of the plurality of radial projections 38b.

With this structure, manually rotating the U-D bent state holding knob 7UD causes the male screw ring 32 to rotate with the U-D bent state holding knob 7UD about the axis of the male screw ring 32. This rotation of the male screw ring 32 causes the female screw ring 35, which is screw-engaged with the male screw ring 32 at the portion of engagement N, and the metal disk 37, which is integral with the female screw ring 35, to move in the axial direction without rotating about the axis of the supporting column 10, so that the distance between the radial plate spring 38 and the metal disk 37 changes.

In such a U-D bent state holding mechanism that is composed of the elements 30 through 38, when the U-D bent state holding knob 7UD is at one of the opposite ends (free-state end) of the range of rotation of the U-D bent state holding knob 7UD, a slight clearance is formed between the radial plate spring 38 and the metal disk 37 as shown in a left half of the drawing in FIG. 3 so that the radial plate spring 38 and the metal disk 37 are not in sliding contact with each other. Therefore, the metal disk 37 and the radial plate spring 38 exert no frictional resistance on the rotating operation of the bendable portion U-D control mechanism.

Rotating the U-D bent state holding knob 7UD to the other end (lock end) of the range of rotation thereof causes the metal disk 37 to move in a direction to be pressed against the radial plate spring 38 as shown in a right half of the drawing in FIG. 3 so that the radial plate spring 38 and the metal disk 37 come in sliding contact with each other. The frictional resistance caused by this sliding contact acts on the rotating operation of the bendable portion U-D control mechanism.

When the magnitude of this frictional resistance is adjusted, firstly the female screw ring 35, which serves as a performance characteristic adjusting member, is rotated to move to an appropriate position in the axial direction relative to the metal disk 37 after each set screw 36 is loosened, and thereafter each set screw 36 is tightened to fix the female screw ring 35 to the metal disk 37 to make the female screw ring 35 integral with the metal disk 37.

This adjustment causes the axial position of the female screw ring 35, which is screw-engaged with the male screw ring 32 at the screw-engaging portion N, relative to the position of rotation of the U-D bent state holding knob 7UD to change, and in turn causes the relative position between the metal disk 37 relative to the radial plate spring 38 in the axial direction to change, to thereby change the magnitude of the frictional resistance produced between the metal disk 37 and the radial plate spring 38.

The R-L tubular drive shaft 11 is provided at the outer end thereof (upper end as viewed in FIG. 3) with an R-L-bending drive disk (second bending drive disk) 22' formed as an integral part of the R-L tubular drive shaft 11. The R-L-bending drive disk 22' has a sufficient size so as to fully close an inward opening (lower opening as viewed in FIG. 3) of the R-L control knob 5RL that is positioned on the inward side (lower side as viewed in FIG. 3) of the internal space of the R-L control knob 5RL. The U-D-bending drive disk 22' is provided on the outer periphery thereof with a plurality of projections 22a' (only one of them is shown in FIG. 3) which project radially outwards to be slidably engaged in a plurality of axial grooves 52 (only one of them is shown in FIG. 3), respectively, which are formed on an inner peripheral surface of the R-L control knob 5RL to be parallel to the axis thereof. Due to the engagements of the plurality of projections 22a' with the plurality of axial grooves 52, respectively, the R-L control knob 5RL rotates with the R-L-bending drive disk 22' (and the R-L tubular drive shaft 11).

Figure 8:
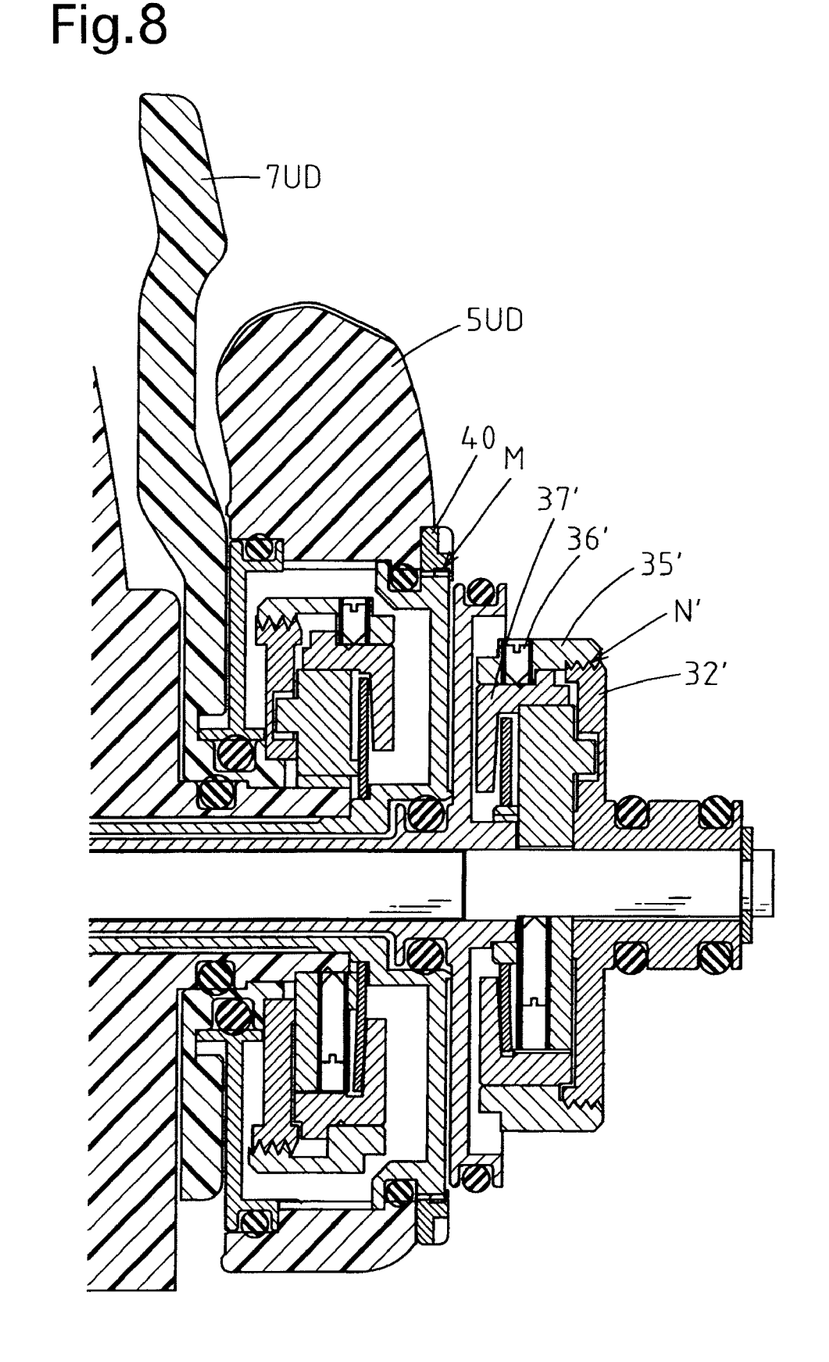
FIG. 8 is an axial cross sectional view of a portion of the endoscope shown in FIG. 2, showing a state where the R-L control knob and the R-L bent state holding knob of the bendable portion control mechanism are removed to adjust frictional resistance which is exerted on the rotating operation of the R-L control knob to hold a bent state of the bendable portion in the rightward/leftward direction.

Reference numerals 30' through 38' shown in FIGS. 3 and 8 designate elements of an R-L bent state holding mechanism which exerts frictional resistance on the rotating operation of the bendable portion R-L control mechanism to hold the bendable portion R-L control mechanism (which includes the R-L control knob 5RL, and the R-L tubular drive shaft 11 and the R-L-bending drive disk 22' that are connected to the R-L control knob 5RL) at any given rotation position. The elements 30' through 38' of the R-L bent state holding mechanism are accommodated and arranged in the internal space of the R-L control knob 5RL which is sealed with O-rings in a watertight fashion to prevent the entry of water into the internal space from the outside. The R-L bent state holding mechanism can operate to exert friction on the rotating operation of the bendable portion R-L control mechanism and to stop exerting the same thereon by operating the R-L bent state holding knob 7RL. The elements 30' through 38' of the R-L bent state holding mechanism which are similar in structure to the elements 30 through 38 of the U-D bent state holding mechanism, so that the descriptions of the elements 30' through 38' are omitted. A resilient C-shaped ring or a circlip is fitted into a groove made in the supporting column 10 at the outer end thereof to prevent the elements 30' through 38' of the R-L bent state holding mechanism from moving in the axial direction of the supporting column 10.

Figure 7:
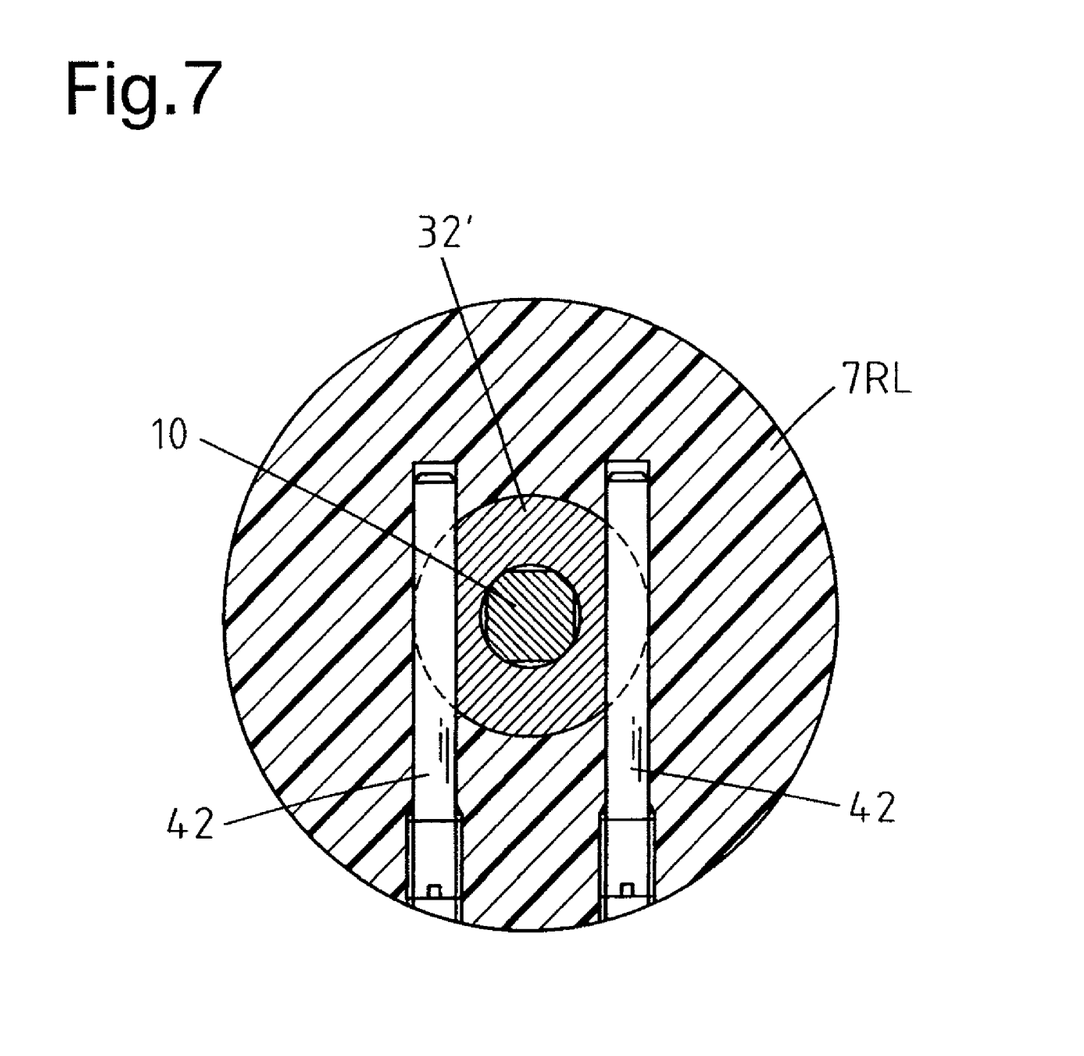
FIG. 7 is a cross sectional view taken along the VII-VII line shown in FIG. 3.

As shown in FIG. 7, which shows a cross sectional view taken along the VII-VII line shown in FIG. 3, the R-L bent state holding knob 7RL is fixed to the head portion of a male screw ring 32' of the R-L bent state holding mechanism by two set screws 42 that are inserted into the R-L bent state holding knob 7RL from a side thereof. If the two set screws 42 are removed, the R-L bent state holding knob 7RL can be removed from the male screw ring 32'.

As shown in FIG. 3, the R-L control knob 5RL, which is engaged with the R-L-bending drive disk 22' to be slidable thereon in the axial direction, is prevented from sliding on the R-L-bending drive disk 22' in the axial direction by the R-L bent state holding knob 7RL. Namely, the R-L bent state holding knob 7RL serves as a retainer which prevents the R-L control knob 5RL from coming off the R-L-bending drive disk 22'.

Manually rotating the R-L bent state holding knob 7RL causes the male screw ring 32' to rotate with the R-L bent state holding knob 7RL about the axis of the male screw ring 32'. This rotation of the male screw ring 32' causes the female screw ring 35', which is screw-engaged with the male screw ring 32' at the portion of engagement N', and the metal disk 37', which is integral with the female screw ring 35', to move in the axial direction without rotating about the axis of the supporting column 10, so that the distance between the radial plate spring 38' and the metal disk 37' changes.

This change of the distance between the radial plate spring 38' and the metal disk 37' causes the axial position of the female screw ring 35', which is screw-engaged with the male screw ring 32' at the screw-engaging portion N', relative to the position of rotation of the R-L bent state holding knob 7RL to change, and this changes causes the relative position between the metal disk 37' relative to the radial plate spring 38' in the axial direction to change to thereby change the magnitude of the frictional resistance produced between the metal disk 37' and the radial plate spring 38'.

The U-D control knob 5UD and the retaining nut 40 are formed so that the inner diameters thereof are greater than the outer diameter of the R-L-bending drive disk 22' and the outer diameter of the R-L bent state holding mechanism (that is composed of the elements 30' through 38'). Therefore, if the R-L control knob 5RL is removed from the R-L-bending drive disk 22', the U-D control knob 5UD and the retaining nut 40 can be removed by moving the R-L control knob 5RL in the axial direction while sliding on the R-L-bending drive disk 22'.

In the present embodiment of the bendable portion control mechanism that is constructed in this manner, when the magnitude of the frictional resistance which is produced by the R-L bent state holding mechanism (the elements 30' through 38') to exert frictional resistance on the rotating operation of the bendable portion R-L control mechanism is adjusted, firstly the R-L bent state holding knob 7RL is removed, and subsequently the R-L control knob 5RL is removed by moving the same in the axial direction before adjustment as shown in FIG. 8.

Upon the removal of the R-L bent state holding knob 7RL and the R-L control knob 5RL, the female screw ring 35' and the head portions of the three set screws 36' (only one of them is shown in FIG. 8), which are screw-engaged in the female screw ring 35', are outwardly exposed. In this state, to adjust the magnitude of the frictional resistance which is produced between the metal disk 37' and the radial plate spring 38' to hold the bendable portion R-L control mechanism, firstly the female screw ring 35', which serves as a performance characteristic adjusting member, is rotated to move to an appropriate position in the axial direction relative to the metal disk 37' after each set screw 36' is loosened with the use of a jig (not shown), and thereafter each set screw 36' is tightened to fix the female screw ring 35' to the metal disk 37' to thereby complete the adjustment.

Figure 1:
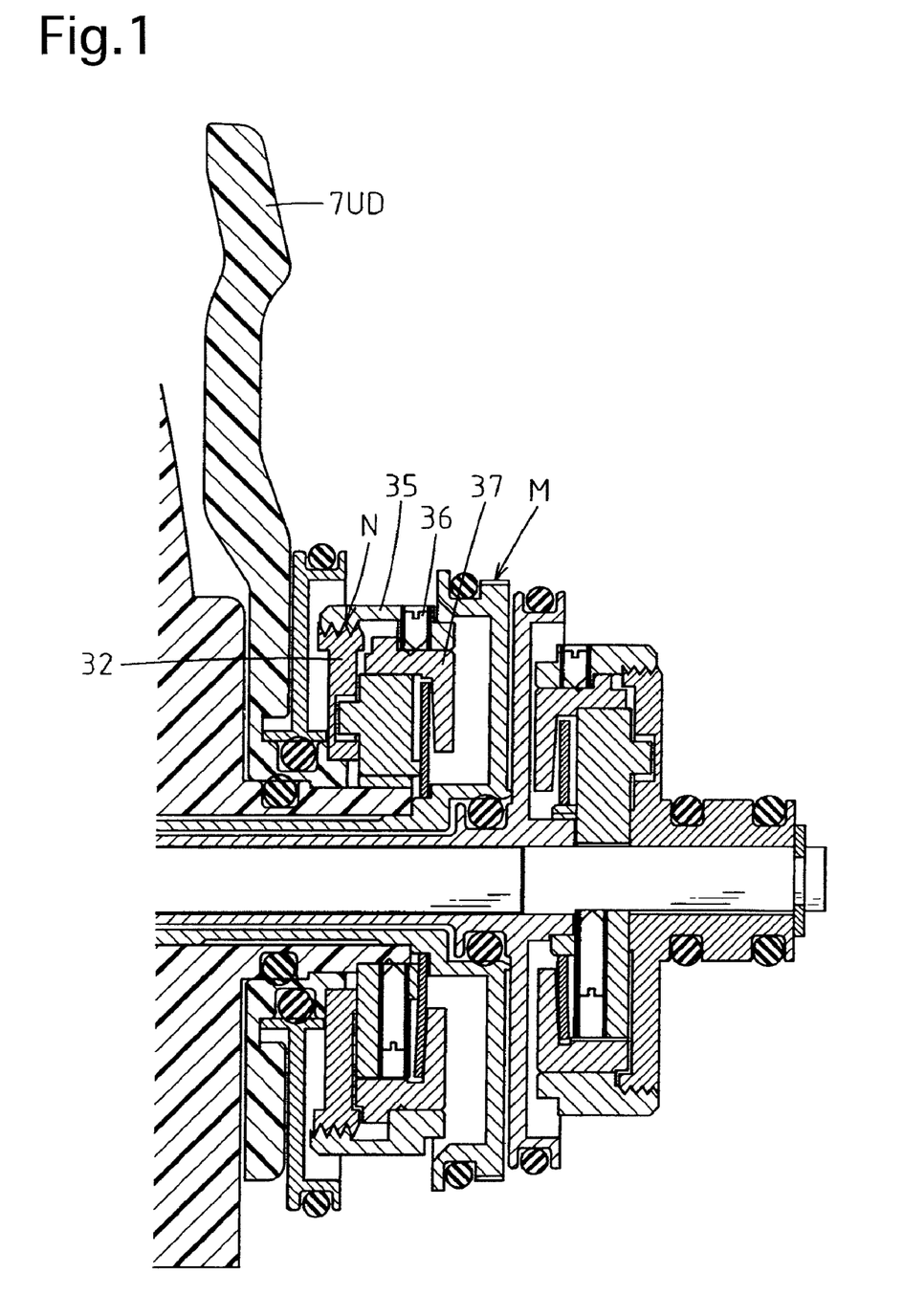
FIG. 1 is an axial cross sectional view of a portion of an embodiment of an endoscope according to the present invention, showing a state where the U-D control knob, the R-L control knob and the R-L bent state holding knob of the bendable portion control mechanism are removed to adjust frictional resistance which is exerted on the rotating operation of the U-D control knob to hold a bent state of the bendable portion in the upward/downward direction.

Additionally, when the magnitude of the frictional resistance which is produced by the U-D bent state holding mechanism (the elements 30 through 38) to exert frictional resistance on the rotating operation of the bendable portion U-D control mechanism is adjusted, firstly the retaining nut 40, which presses the U-D control knob 5UD to fix the same to the U-D tubular drive shaft 12, is loosened and removed and subsequently the U-D control knob 5UD is removed by moving the same in the axial direction before adjustment as shown in FIG. 1. At this time, only the U-D control knob 5UD and the retaining nut 40 can be removed in the axial direction without interfering with any of the elements 30' through 38' of the R-L bent state holding mechanism (i.e., with no necessity to disassemble the R-L bent state holding mechanism) since the inner diameters of the U-D control knob 5UD and the retaining nut 40 are greater than the outer diameter of the R-L-bending drive disk 22' and the outer diameter of the R-L bent state holding mechanism that is composed of the elements 30' through 38'.

Upon the removal of the U-D control knob 5UD and the retaining nut 40, the female screw ring (performance characteristic adjusting member) 35 and the head portions of the three set screws 36 (only one of them is shown in FIG. 1), which are screw-engaged in the female screw ring 35, are outwardly exposed. In this state, to adjust the magnitude of the frictional resistance which is produced between the metal disk 37 and the radial plate spring 38 to hold the bendable portion U-D control mechanism, firstly the female screw ring 35 is rotated to move to an appropriate position in the axial direction relative to the metal disk 37 after each set screw 36 is loosened with the use of a jig (not shown), and thereafter each set screw 36 is tightened to fix the female screw ring 35 to the metal disk 37 to thereby complete the adjustment.

Therefore, when it is necessary to check whether or not the bendable portion is in an appropriate bent state, the U-D control knob 5UD can be easily removed as many times as desired, so that the magnitude of the frictional resistance which is produced by the U-D bent state holding mechanism (the elements 30 through 38) can be easily adjusted. When such an adjustment operation is performed, there is no need to disassemble and even touch the R-L bent state holding mechanism (the elements 30' through 38') at all; moreover, it is not required to readjust the magnitude of the frictional resistance which is produced by the R-L bent state holding mechanism (the elements 30' through 38'), which is labor-saving.

As can be understood from the foregoing, the present embodiment of the bendable portion control mechanism of the endoscope according to the present invention is configured so that the two control knobs 5UD and 5RL can be detached from and attached to the control portion 4 of the endoscope with no need to disassemble either the U-D bent state holding mechanism (the elements 30 through 38) or the R-L bent state holding mechanism (the elements 30' through 38'), and so that the magnitude of the frictional resistance which is produced by the U-D bent state holding mechanism (the elements 30 through 38) and the magnitude of the frictional resistance which is produced by the R-L bent state holding mechanism (the elements 30' through 38') can be adjusted simply by removing the two control knobs 5UD and 5RL.

The present invention is not limited solely to the above described particular embodiment. For instance, the arrangement of the two control knobs 5UD and 5RL can be reversed.

Obvious changes may be made in the specific embodiment of the present invention described herein, such modifications being within the spirit and scope of the invention claimed. It is indicated that all matter contained herein is illustrative and does not limit the scope of the present invention.

What is claimed is:

1. A bendable portion control mechanism of an endoscope including a control portion and an insertion portion extending from said control portion, said insertion portion having a bendable portion, said bendable portion control mechanism comprising:
    two manually-rotatable control knobs, one of said manually-rotatable control knobs being provided on top of the other thereof and disposed coaxially with each other on said control portion, for bending said bendable portion in two orthogonal directions, each of said control knobs including a water-sealed internal space;
    two bent state holding mechanisms, provided in said two water-sealed internal spaces, respectively, for holding a bent state of said bendable portion in said two orthogonal directions by exerting frictional resistance on rotating operations of said two control knobs,
    wherein said two control knobs are configured to be detached from and attached to said control portion while said two bent state holding mechanisms are attached to said control portion, and
    wherein it is possible to adjust operational characteristics of each of said two bent state holding mechanisms upon detaching said two control knobs, respectively; and
    a first bending drive disk mounted to said control portion to be freely rotatable,
    wherein one of said control knobs which is positioned closest to a base of said control portion is disengageably engaged with an outer peripheral part of said first bending drive disk in a direction of a common rotational axis of said control knobs, and
    wherein said one of said control knobs is fixed to said first bending drive disk by a retaining nut which is screw-engaged with an outer peripheral part of said first bending drive disk.

2. The bendable portion control mechanism according to claim 1, further comprising a second bending drive disk mounted to said control portion to be freely rotatable,
    wherein said other of said control knobs is engaged with an outer peripheral part of said second bending drive disk to be freely disengaged therefrom in said direction of said common rotation axis of said control knobs, and
    wherein said one of said control knobs and said retaining nut are formed so that inner diameters thereof are greater than an outer diameter of said second bending drive disk and an outer diameter of one of said two bent state holding mechanisms which is positioned in said other of said control knobs.

3. The bendable portion control mechanism according to claim 1, wherein one of said two bent state holding mechanisms, which is positioned in one of said control knobs which is positioned closest to a base of said control portion, comprises a performance characteristic adjusting member for exerting frictional resistance on said rotating operation of said one of said control knobs, and
    wherein said performance characteristic adjusting member is outwardly exposed when said one of said control knobs is detached.

4. The bendable portion control mechanism according to claim 1, further comprising at least two control wires, distal ends of which are fixed to said bendable portion, and are extended to said control portion through said insertion portion,
    wherein said two control knobs pull said two control wires to bend said bendable portion in said two orthogonal directions, respectively, when manually rotated.

5. The bendable portion control mechanism according to claim 1, further comprising:
    a stationary cylindrical shaft which extends upright from said control portion to be coaxial with said common rotational axis of said two control knobs; and
    a tubular drive shaft positioned over said stationary cylindrical shaft to be freely rotatable on an axis of said stationary cylindrical shaft,
    wherein said first bending drive disk is formed integral with said tubular drive shaft.

6. The bendable portion control mechanism according to claim 2, further comprising:
    a stationary cylindrical shaft which extends upright from said control portion to be coaxial with said common rotational axis of said two control knobs;
    an inner tubular drive shaft positioned over said stationary cylindrical shaft to be freely rotatable on an axis of said stationary cylindrical shaft; and
    an outer tubular drive shaft positioned over said inner tubular drive shaft to be freely rotatable on said axis of said stationary cylindrical shaft,
    wherein said first bending drive disk and said second bending drive disk are formed integral with said outer tubular drive shaft and said inner tubular drive shaft, respectively.

7. The bendable portion control mechanism according to claim 2, wherein said first bending drive disk and said second bending drive disk are positioned between said two control knobs so as to face each other.

8. The bendable portion control mechanism according to claim 1, further comprising at least one O-ring positioned between said first bending drive disk and said one of said two control knobs to seal said water-sealed internal space thereof in a watertight fashion.

9. The bendable portion control mechanism according to claim 2, further comprising:
    at least one O-ring positioned between said first bending drive disk and said one of said two control knobs to seal said water-sealed internal space thereof in a watertight fashion; and
    at least one O-ring positioned between said second bending drive disk and said other of said two control knobs to seal said water-sealed internal space thereof in a watertight fashion.

* * * * *